United States Patent [19]

Snyder et al.

[11] Patent Number: 5,577,507
[45] Date of Patent: Nov. 26, 1996

[54] COMPOUND LENS FOR ULTRASOUND TRANSDUCER PROBE

[75] Inventors: Jonathan E. Snyder, Whitefish Bay; Leslie J. Keres, Waukesha, both of Wis.; Gregg W. Frey, East Wenatchee, Wash.

[73] Assignee: General Electric Company, Milwaukee, Wis.

[21] Appl. No.: 343,078

[22] Filed: Nov. 21, 1994

[51] Int. Cl.$^6$ ........................................... A61B 8/00
[52] U.S. Cl. ........................................... 128/663.01
[58] Field of Search ..................... 128/662.03, 662.06, 128/660.1, 663.01; 73/642, 644; 367/150

[56] References Cited

U.S. PATENT DOCUMENTS 4,387,720   6/1983   Miller ..................... 128/663.01
4,699,150  10/1987   Kawabuchi et al. ........ 128/663.01 X
4,862,893   9/1989   Martinelli .................. 128/662.03

Primary Examiner—Francis Jaworski
Attorney, Agent, or Firm—Dennis M. Flaherty; John H. Pilarski

[57] ABSTRACT

A compound lens for focusing ultrasound emitted from an ultrasound probe having an array of piezoelectric transducer elements. The compound lens has an inner lens part with a convex cylindrical front face and a rear face which is acoustically coupled to the front face of the transducer array, and an outer lens part with a concave cylindrical rear face which is acoustically coupled to the convex cylindrical front face of the inner lens part. The inner lens part may be in the form of a conventional silicone rubber focusing lens. The outer lens part is made of an acoustic medium having a higher acoustic velocity and greater durability than silicone rubber, e.g., polymethylpentene, nylon and high-density polyethylene. Also the outer lens part has greater chemical resistance than silicone rubber.

7 Claims, 2 Drawing Sheets

COMPOUND LENS FOR ULTRASOUND TRANSDUCER PROBE

FIELD OF THE INVENTION

This invention generally relates to probes used in ultrasonic imaging of the human anatomy. In particular, the invention relates to the construction of lenses for focusing the ultrasound transmitted by the piezoelectric transducer elements of an ultrasound probe.

BACKGROUND OF THE INVENTION

A conventional ultrasonic probe comprises a transducer package which must be supported within a probe housing 2. As shown in FIG. 1, a conventional transducer package comprises an array 4 of narrow transducer elements. Each transducer element is made of piezoelectric ceramic material. The piezoelectric material is typically lead zirconate titanate (PZT), polyvinylidene difluoride, or PZT ceramic/polymer composite.

Typically, each transducer element has a metallic coating on opposing front and back faces to serve as electrodes. The metallic coating on the front face serves as the ground electrode. The ground electrodes of the transducer elements are all connected to a common ground. The metallic coating on the back face serves as the signal electrode. The signal electrodes of the transducer elements are connected to respective electrical conductors formed on a flexible printed circuit board (PCB) 6.

During operation, the signal and ground electrodes of the piezoelectric transducer elements are connected to an electrical source having an impedance $Z_s$. When a voltage waveform is developed across the electrodes, the material of the piezoelectric element contracts at a frequency corresponding to that of the applied voltage, thereby emitting an ultrasonic wave into the media to which the piezoelectric element is coupled. Conversely, when an ultrasonic wave impinges on the material of the piezoelectric element, the latter produces a corresponding voltage across its terminals and the associated electrical load component.

In conventional applications, each transducer element produces a burst of ultrasonic energy when energized by a pulsed waveform produced by a transmitter (not shown). The pulses are transmitted to the transducer elements via the flexible PCB 6. This ultrasonic energy is transmitted by the probe into the tissue of the object under study. The ultrasonic energy reflected back to transducer element array 4 from the object under study is converted to an electrical signal by each receiving transducer element and applied separately to a receiver (not shown).

The transducer package also comprises a mass of suitable acoustical damping material having high acoustic losses, e.g., silver epoxy, positioned at the back face of the transducer element array 4. This backing layer 8 is coupled to the rear face of the transducer elements to absorb ultrasonic waves that emerge from the back side of each element so that they will not be partially reflected and interfere with the ultrasonic waves propagating in the forward direction.

In the transmission mode, the piezoelectric ceramic of the transducer elements alternately contracts and expands in response to electrical signals received from a pulser circuit (not shown) via coaxial cables (not shown) electrically connected to the flexible PCB 6. The resulting compression waves propagate in both the forward and rearward directions, with the rearward-propagating compression waves being damped by the backing layer 8.

In the receiving mode, the piezoelectric ceramic of the transducer elements alternately compresses and expands in response to compression waves reflected back to the probe by the object being ultrasonically examined. These waves are transduced into electrical signals which are carried to a receiver circuit (not shown) by the flexible PCB 6 and the coaxial cable connected thereto.

The transducer element array 4, flexible PCB 6 and backing layer 8 are bonded together in a stack-up arrangement which is secured inside a four-sided array case 10, which protects the fragile transducer elements during probe assembly. The perimeter of the array case 10 may be surrounded with a sheet of electrically conductive foil to form an electrical shield 20. The transducer package or stack is mounted inside the probe housing 2 with internal spaces filled with potting material 18.

Typically, a first acoustic impedance matching layer 12 is laminated to the bottom surface of the transducer array, as shown in FIG. 1. Optionally, a second acoustic impedance matching layer 14 can be laminated to the first acoustic impedance matching layer 12. These impedance matching layers transform the high acoustic impedance of the transducer elements to the low acoustic impedance of the human body or water, thereby improving the coupling with the medium in which the emitted ultrasonic waves will propagate.

The front face of the outermost acoustic impedance matching layer is conventionally bonded to the planar rear face of a positive cylindrical lens 16 using an acoustically transparent thin layer of silicone adhesive. The front face of the lens has a convex cylindrical contour which focuses the ultrasound emitted from the outermost acoustic impedance matching layer. Two conventional lens geometries are depicted in FIGS. 2A and 2B.

Lens 16 is conventionally made of silicone rubber. This layer of silicone rubber serves three purposes: (1) acoustic focusing (due to its lens-shaped cross section and its low acoustic velocity material properties); (2) providing a chemical barrier to protect the transducer elements from attack by gels, body fluids, cleaning agents, etc.; and (3) providing an electrical barrier to protect the patient from the electrically active transducer elements.

Although a lens made of silicone rubber will adequately serve the above-described functions of an outer layer, the outer surface of the silicone rubber is easily damaged by abrasion, impact and some harsh chemicals commonly used in clinical environments. Such damage to the outer layer of the transducer package may result in a loss of acoustic focusing integrity and/or breach of the chemical/electrical barrier, thereby causing irreparable probe damage and/or patient safety concerns.

SUMMARY OF THE INVENTION

The present invention solves the problem of the susceptibility of silicone rubber to damage by providing a compound lens in which the outer layer is made of an acoustic medium which is more durable than silicone rubber. The compound lens comprises an inner lens part having a convex cylindrical front face and a rear face acoustically coupled to the front face of an array of piezoelectric transducer elements, and an outer lens part having a concave cylindrical rear face acoustically coupled to the convex cylindrical front face of the inner lens part. The outer lens part is made of a first acoustic medium having a first acoustic velocity and the inner lens part is made of silicone rubber or some other acoustic medium having a second acoustic velocity which is less than the first acoustic velocity. Preferably, the material of the outer protective lens part is more durable and has greater chemical resistance than silicone rubber has. Since the outer lens part is made of an acoustic material which is more durable than silicone rubber, its front face will be less susceptible to damage than the front face of a conventional monolithic silicone rubber lens.

In accordance with the preferred embodiment of the invention, the inner lens part has a positive cylindrical lens shape and the outer lens part has a conforming negative cylindrical lens shape, i.e., the contour of the convex cylindrical front face of the inner lens part matches the contour of the concave cylindrical rear face of the inner lens part, allowing the inner lens part to nest in the outer lens part. The inner and outer lens parts can be bonded along this interface using an acoustically transparent thin layer of adhesive. The contour is selected such that the ultrasound will be focused when it propagates across the interface from the low-acoustic-velocity inner lens part into the high-acoustic-velocity outer lens part.

In accordance with another preferred embodiment of the invention, a compound lens can be bonded directly to the front face of the transducer element array, i.e., without any acoustic impedance matching layers therebetween. Such a construction reduces the costs of manufacture and simplifies the transducer stack assembly process.

DETAILED DESCRIPTION OF THE PREFERRED EMBODIMENTS

Figure 1:
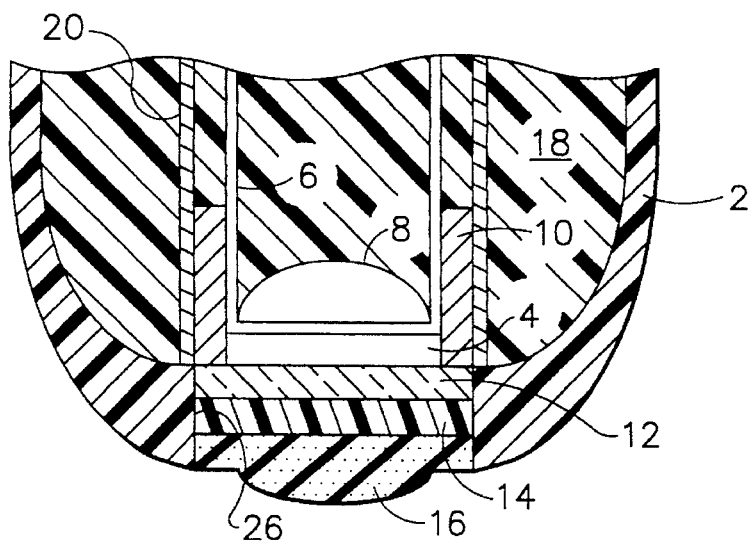
FIG. 1 is a schematic sectional view of a conventional transducer stack-up installed in an ultrasound probe housing.
Figure 2A:
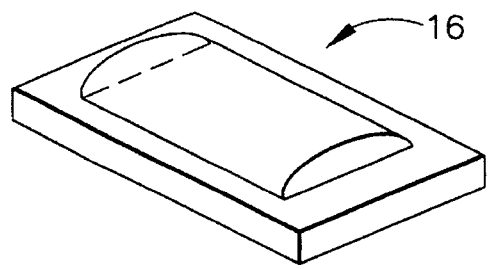
FIGS. 2A and 2B are isometric views of respective conventional silicone rubber lenses having a positive cylindrical lens shape for focusing acoustic energy.
Figure 2B:
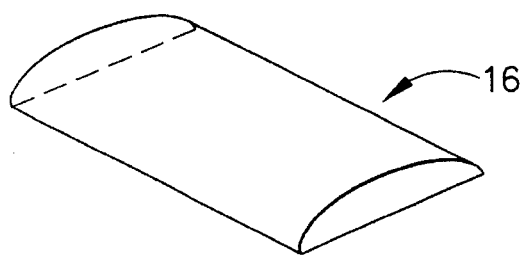
Figure 3:
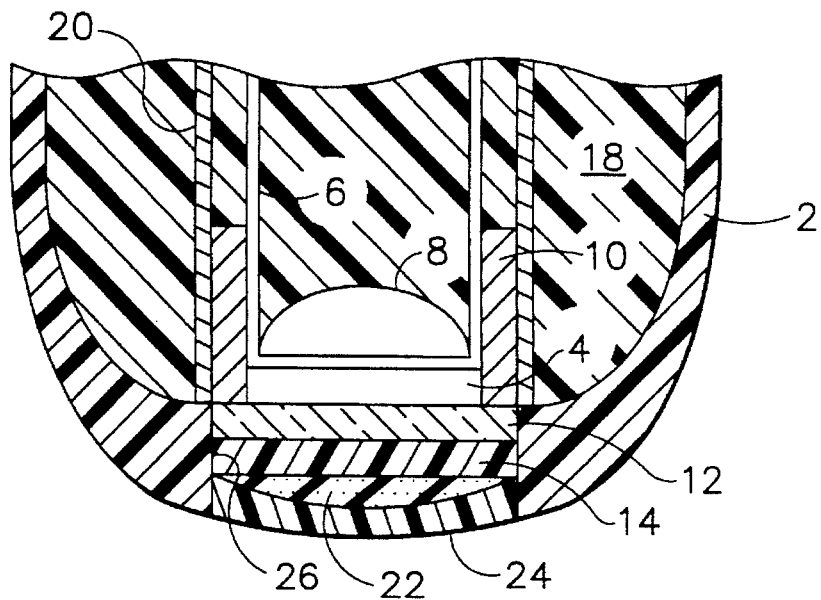
FIG. 3 is a schematic sectional view of one preferred embodiment of the invention in which a compound acoustic lens is bonded to the front face of an acoustic impedance matching layer in an ultrasound probe.

Referring to FIG. 3, an ultrasonic transducer stack in accordance with one preferred embodiment of the invention has a compound lens in place of the conventional monolithic silicone rubber lens, but is otherwise similar in construction to the conventional transducer stack shown in FIG. 1. The transducer element array 4 is mounted inside an array case 10 with a backing layer 8 of acoustic damping material acoustically coupled to the rear face of the array. An inner acoustic impedance matching layer 12 is acoustically coupled to the front face of transducer array 4. An outer acoustic impedance matching layer 14 is acoustically coupled to the inner acoustic impedance matching layer 12.

In accordance with the preferred embodiment shown in FIG. 3, a compound lens comprises an inner lens part 22 and an outer lens part 24. The outer lens part is made from an acoustic medium having a relatively higher acoustic velocity; the inner lens part is made from an acoustic medium having a relatively lower acoustic velocity. The inner lens part 22 has a convex cylindrical front face 22a and a rear face 22b acoustically coupled to the front face of inner acoustic impedance matching layer 14. The outer lens part 24 has a concave cylindrical rear face 24b acoustically coupled to the convex cylindrical front face 22a of inner lens part 22. A suitable material for the inner lens part is silicone rubber or urethane. Suitable materials for the outer lens part include polymethylpentene, nylon and high-density polyethylene.

In accordance with the invention, the inner lens part 22 has a positive cylindrical lens shape and the outer lens part 24 has a conforming negative cylindrical lens shape. The opposing concave cylindrical rear face 24b of outer lens part 24 and convex cylindrical front face 22a of inner lens part 22 form an interface. The inner and outer lens parts are bonded along this interface using an acoustically transparent thin layer of adhesive. The contour of the opposing faces is selected such that ultrasound waves emitted from the transducer array are focused toward the plane of symmetry of the lens, e.g., the opposing concave cylindrical rear face 24b of outer lens part 24 and the convex cylindrical front face 22a of inner lens part 22 may each have a parabolic cylindrical shape.

To the extent that additional acoustic focusing is desired, the front face 24b of outer lens part 24 of the compound lens can also have a cylindrical shape with a contour determined by the position of the focal point desired. Since the outer lens part is made of an acoustic material which is more durable than silicone rubber, its front face will be less susceptible to damage than the front face of conventional monolithic silicone rubber lenses.

The entire transducer stack, including the compound lens, is secured by adhesive inside an aperture formed in the tip of probe housing 2. For example, outer lens part 24 may be formed with planar side walls 24c and 24d (shown in FIG. 3) and planar end walls (not shown) which are respectively bonded to the side and end walls of a rectangular aperture 26 formed in the probe tip. Alternatively, the lens and the probe housing could be formed as an integral unit.

Figure 4:
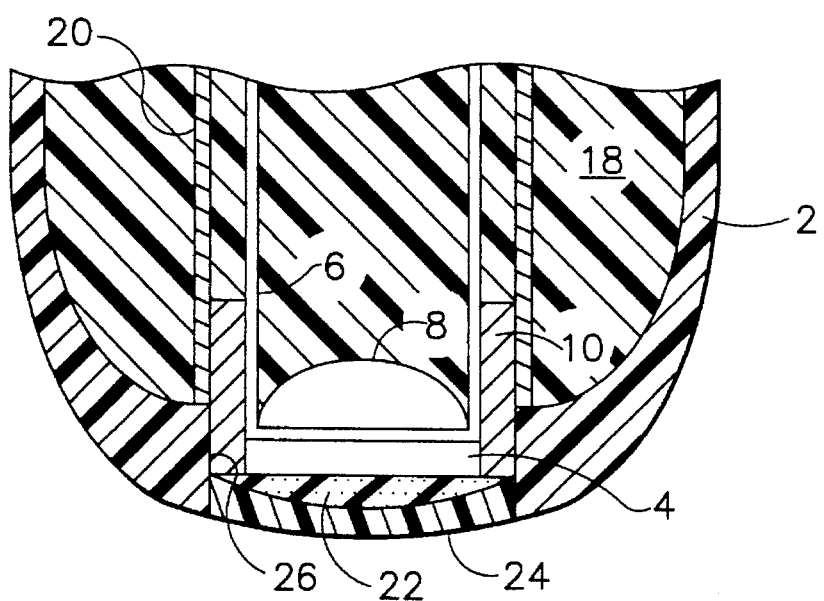
FIG. 4 is a schematic sectional view of another preferred embodiment of the invention in which a compound acoustic lens is bonded to the front face of the transducer element array in an ultrasound probe.

In accordance with another preferred embodiment shown in FIG. 4, a compound lens, constructed as described above, is bonded directly to the front face of the transducer array 4, i.e., without any acoustic impedance matching layers therebetween. Such a construction reduces the costs of manufacture and simplifies the transducer stack assembly process.

The foregoing preferred embodiments have been disclosed for the purpose of illustration. Variations and modifications which do not depart from the broad concept of the invention will be readily apparent to those skilled in the design of ultrasonic probes. In particular, the inner lens part of the compound lens need not be made of silicone rubber, provided that the inner lens part has an acoustic velocity less than the acoustic velocity of the outer lens part. All such variations and modifications are intended to be encompassed by the claims set forth hereinafter.

We claim:

1. An ultrasound probe comprising:

a planar array of piezoelectric transducer elements having a front face;

an inner lens part having a convex cylindrical front face and a planar rear face acoustically coupled to said front face of said planar array; and an outer lens part having a concave cylindrical rear face acoustically coupled to said convex cylindrical front face of said inner lens part and having a convex cylindrical front face, wherein said outer lens part is made of a first acoustic medium having a first acoustic velocity greater than the acoustic velocity in human tissue and said inner lens part is made of a second acoustic medium having a second acoustic velocity less than the acoustic velocity in human tissue.

2. The ultrasound probe as defined in claim 1, wherein said first acoustic medium is nylon.

3. The ultrasound probe as defined in claim 1, wherein said first acoustic medium is polymethylpentene.

4. The ultrasound probe as defined in claim 1, wherein said first acoustic medium is high-density polyethylene.

5. The ultrasound probe as defined in claim 1, wherein said second acoustic medium is silicone rubber.

6. The ultrasound probe as defined in claim 1, wherein said inner lens part is acoustically coupled to said front face of said planar array via at least one acoustic impedance matching layer.

7. The ultrasound probe as defined in claim 1, wherein said inner lens part is bonded to said front face of said planar array via an acoustically transparent layer of adhesive.

* * * * *